US009400255B2

(12) United States Patent
Nohara et al.

(10) Patent No.: US 9,400,255 B2
(45) Date of Patent: Jul. 26, 2016

(54) X-RAY FLUORESCENCE SPECTROMETER COMPRISING A GAS BLOWING MECHANISM

(71) Applicant: Hitachi High-Tech Science Corporation, Minato-ku, Tokyo (JP)

(72) Inventors: Hiroaki Nohara, Tokyo (JP); Yoshiki Matoba, Tokyo (JP); Noriaki Sakai, Tokyo (JP); Toshitada Takeuchi, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 199 days.

(21) Appl. No.: 14/219,579

(22) Filed: Mar. 19, 2014

(65) Prior Publication Data
US 2014/0294143 A1  Oct. 2, 2014

(30) Foreign Application Priority Data
Mar. 28, 2013  (JP) ................. 2013-068420

(51) Int. Cl.
*G01N 23/223* (2006.01)

(52) U.S. Cl.
CPC ........ *G01N 23/223* (2013.01); *G01N 2223/076* (2013.01)

(58) Field of Classification Search
CPC .. G01N 23/223; G01N 2223/076; H01J 35/18
USPC ............................. 378/44–50, 161
See application file for complete search history.

(56) References Cited

U.S. PATENT DOCUMENTS

| 3,889,113 | A | * | 6/1975 | Rhodes | G01N 23/223 378/193 |
| 5,740,223 | A | * | 4/1998 | Ozawa | G01N 23/223 378/161 |
| 6,012,325 | A | * | 1/2000 | Ma | G01N 15/0618 378/47 |
| 6,052,429 | A | * | 4/2000 | Ohno | G01N 23/223 378/161 |
| 6,233,307 | B1 | * | 5/2001 | Golenhofen | G01N 23/207 378/44 |
| 6,337,897 | B1 | * | 1/2002 | Kawahara | G01N 23/223 378/148 |
| 6,370,220 | B1 | * | 4/2002 | Stoop | G01N 23/223 378/45 |
| 6,421,414 | B1 | * | 7/2002 | Huber | G01N 23/223 378/45 |
| 6,442,231 | B1 | * | 8/2002 | O'Hara | G01N 23/20025 378/145 |
| 6,479,818 | B1 | * | 11/2002 | McCarthy | G01N 23/083 250/307 |

(Continued)

FOREIGN PATENT DOCUMENTS

JP  2011-203102 A  10/2011

*Primary Examiner* — Allen C. Ho
(74) *Attorney, Agent, or Firm* — Banner & Witcoff, Ltd.

(57) ABSTRACT

An X-ray fluorescence spectrometer includes: a sample stage configured to place a sample thereon; an X-ray source configured to irradiate the sample with primary X-rays; a detector, which is configured to detect fluorescent X-rays produced from the sample irradiated with the primary X-rays, and which includes an X-ray incident window formed by a window material through which fluorescent X-rays is transmittable; and a gas blowing mechanism configured to blow a gas to at least one of an outer surface of the X-ray incident window and the sample stage.

8 Claims, 2 Drawing Sheets

(56) References Cited

U.S. PATENT DOCUMENTS

| | | | |
|---|---|---|---|
| 6,577,704 B1 * | 6/2003 | Holz | G01N 23/2076 378/44 |
| 6,754,304 B1 * | 6/2004 | Kumakhov | G01N 23/223 378/45 |
| 6,965,663 B2 * | 11/2005 | Ohzawa | G01N 23/223 250/505.1 |
| 7,065,174 B2 * | 6/2006 | Sipila | G01N 23/223 378/44 |
| 7,072,439 B2 * | 7/2006 | Radley | G01N 23/12 378/47 |
| 7,233,643 B2 * | 6/2007 | Sipila | G01N 23/223 378/44 |
| 7,313,220 B2 * | 12/2007 | Katz | G01N 23/223 378/44 |
| 7,428,293 B2 * | 9/2008 | Fukai | G01N 23/223 378/147 |
| 7,688,942 B2 * | 3/2010 | Klein | G01N 23/223 250/400 |
| 7,970,101 B2 * | 6/2011 | Sakai | G01N 23/223 378/44 |
| 8,000,439 B2 * | 8/2011 | Matoba | G01N 23/223 378/44 |
| 8,019,048 B2 * | 9/2011 | Sikora | B08B 3/04 378/161 |
| 8,064,570 B2 * | 11/2011 | Tannian | G01N 23/223 378/44 |
| 8,835,857 B2 * | 9/2014 | Eggert | G01T 7/00 250/361 R |
| 8,982,338 B2 * | 3/2015 | Hamilton | G01N 23/223 356/72 |
| 9,057,685 B2 * | 6/2015 | Allen | G01N 23/223 |
| 9,116,106 B2 * | 8/2015 | Goto | G21K 1/02 |
| 9,116,107 B2 * | 8/2015 | Goto | G21K 1/02 |
| 9,182,362 B2 * | 11/2015 | Kantonen | G01N 23/223 |

* cited by examiner

X-RAY FLUORESCENCE SPECTROMETER COMPRISING A GAS BLOWING MECHANISM

This application claims priority from Japanese Patent Application No. 2013-068420 filed on Mar. 28, 2013, the entire subject-matter of which is incorporated herein by reference.

BACKGROUND

1. Technical Field

The disclosure relates to an X-ray fluorescence spectrometer which is configured to perform detection of a hazardous substance or the like, and which is used for, for example, screening products, or measuring the film thickness of plating or the like.

2. Description of the Related Art

In the X-ray fluorescence spectroscopy, a sample is irradiated with X-rays emitted from an X-ray source, and fluorescence X-rays which are characteristic X-rays released from the sample are detected by an X-ray detector. A spectrum is obtained from the energy of the detected X-rays, and the sample is qualitatively or quantitatively analyzed, or the film thickness is measured. In the X-ray fluorescence spectroscopy, a sample can be rapidly analyzed in a non-destructive manner. Therefore, the X-ray fluorescence spectroscopy is widely used in the process and quality management or the like. Recently, the accuracy and sensitivity of the X-ray fluorescence spectroscopy have been improved, so that micro measurement can be performed. The X-ray fluorescence spectroscopy is therefore expected to be in widespread use as an analysis technique for detecting a hazardous substance which may be contained in, specifically, a material, a composite electronic component, or the like.

In such an X-ray fluorescence spectroscopy, when a powdery sulfide material or the like is to be analyzed, the following countermeasure has been taken in order to prevent a detector and an X-ray bulb from corroding. A resin film such as a PET film, which is a so-called MYLAR® film, is disposed in front of the detector and the X-ray bulb, to prevent the sample powder from attaching to them. For example, JP-A-2011-203102 discloses an apparatus in which a sample is placed on a resin film by using a sample holder to which a MYLAR® film is attached, the sample holder is mounted so as to close an opening of a base plate, the sample is irradiated with excited X-rays through the opening and the resin film, and fluorescent X-rays are received.

SUMMARY

The above-described related art has some disadvantages.

In the above-described related-art X-ray fluorescence spectrometer, since a MYLAR® film is used, some of X-rays are absorbed by the MYLAR® film, so that there may cause a disadvantage that the sensitivity is lowered. Specifically, characteristic X-rays are absorbed by the MYLAR® film, and the sensitivity with respect to a light element is reduced. In the case where a sample or the like is attached to the MYLAR® film and the MYLAR® film is contaminated, it is necessary to replace the MYLAR® film with a new one, and there is a further disadvantage that the workability is poor. Moreover, there may be a possibility that fine powder or the like produced during replacement of the MYLAR® film may attach to the beryllium windows of the detector and the X-ray bulb, and a failure may be caused.

Therefore, illustrative aspects of the invention provide an X-ray fluorescence spectrometer that can prevent a sample or the like from attaching to a detector, without using a MYLAR® film.

According to a first illustrative aspect of the invention, there may be provided an X-ray fluorescence spectrometer comprising: a sample stage configured to place a sample thereon; an X-ray source configured to irradiate the sample with primary X-rays; a detector, which is configured to detect fluorescent X-rays produced from the sample irradiated with the primary X-rays, and which comprises an X-ray incident window formed by a window material through which fluorescent X-rays is transmittable; and a gas blowing mechanism configured to blow a gas to an outer surface of the X-ray incident window.

The X-ray fluorescence spectrometer includes the gas blowing mechanism that blows the gas to the outer surface of the X-ray incident window. Therefore, the sample or the like can be prevented from attaching to the X-ray incident window, by the gas that is blown toward the X-ray incident window by the gas blowing mechanism. Since a MYLAR® film is not used, the characteristic X-rays released from the sample is not absorbed by the MYLAR® film. Therefore, the sensitivity and throughput of the analysis are improved.

According to a second illustrative aspect of the invention, in the X-ray fluorescence spectrometer according to the first illustrative aspect, the gas blowing mechanism may comprise a mechanism which also blows the gas to the sample stage.

In the X-ray fluorescence spectrometer, the gas blowing mechanism has a mechanism which blows the gas also to the sample stage, and hence the sample on the sample stage can be suppressed from scattering toward the side of the detector. The gas blowing mechanism is set such that the gas is blown at a speed which does not cause the sample on the sample stage to be blown off.

According to a third illustrative aspect of the invention, in the X-ray fluorescence spectrometer according to the first or the second illustrative aspect, the gas may comprise He.

In the X-ray fluorescence spectrometer, the gas to be blown is He (helium). Since He absorbs less characteristic X-rays than the air, it is possible to obtain a high sensitivity in an analysis of a light element. When, in the second invention, He is selected as the gas to be blown to the sample stage, also the atmosphere around the sample stage is a He atmosphere, and the absorption of characteristic X-rays is reduced. In an analysis of a light element, therefore, a higher sensitivity can be obtained.

According to a fourth illustrative aspect of the invention, in the X-ray fluorescence spectrometer according to any one of the first to third illustrative aspects, the detector may comprise a collimator section, which is disposed in a periphery of the X-ray incident window, and which is configured to set an opening degree of the X-ray incident window, the gas blowing mechanism may comprise: a supply source of the gas; a gas pipe, a base end of which is connected to the supply source; and an internal gas flow passage, which is disposed in the collimator section, and in which a tip end of the gas pipe is connected to a base end of the internal gas flow passage, wherein the internal gas flow passage comprises a plurality of blow out holes for blowing out the gas at a tip end thereof, and the blow out holes may be disposed in the periphery of the X-ray incident window so as to blow out the gas toward the outer surface of the X-ray incident window.

In the X-ray fluorescence spectrometer, the plurality of blow out holes is arranged in the periphery of the X-ray incident window such that the gas can be blown toward the outer surface of the X-ray incident window. When the gas is blown to the X-ray incident window from the plurality of blow out holes arranged in the periphery of the X-ray incident window, therefore, it is possible to effectively suppress the sample or the like from attaching to the whole X-ray incident window. Since the internal gas flow passage is formed in the collimator section, the gas can be blown by the compact configuration. Therefore, the spectrometer can be placed without reducing the degree of freedom in installation of the detector as far as possible.

According to a fifth illustrative aspect of the invention, in the X-ray fluorescence spectrometer according to any one of the first to the fourth illustrative aspects, the detector may comprise a collimator section, which is disposed in a periphery of the X-ray incident window, and which is configured to set an opening degree of the X-ray incident window, and the gas blowing mechanism may comprise an internal gas flow passage, which is disposed in the collimator section, and which is branched off to: a plurality of first holes disposed in the periphery of the X-ray incident window so as to blow out the gas toward the outer surface of the X-ray incident window; and a plurality of second holes opened in a tip end surface of the collimator section 6 so as to blow out the gas toward the sample stage.

According to the illustrative aspects of the invention, the following advantages may be achieved.

The X-ray fluorescence spectrometer of the invention includes the gas blowing mechanism which blows the gas to the outer surface of the X-ray incident window. Therefore, the sample or the like can be prevented from attaching to the X-ray incident window, and the sensitivity and the throughput are improved.

Consequently, the X-ray fluorescence spectrometer is free from the disadvantages which are caused in the case where a MYLAR® film is used. The X-ray incident window, which is always in a satisfactory condition allows a highly sensitive analysis to be performed. Therefore, a stable measurement is enabled in, for example, the screening of products with respect to hazardous substance laws and regulations.

DETAILED DESCRIPTION

Hereinafter, an illustrative embodiment of the X-ray fluorescence spectrometer of the invention will be described with reference to FIGS. 1, 2A and 2B.

Figure 1:
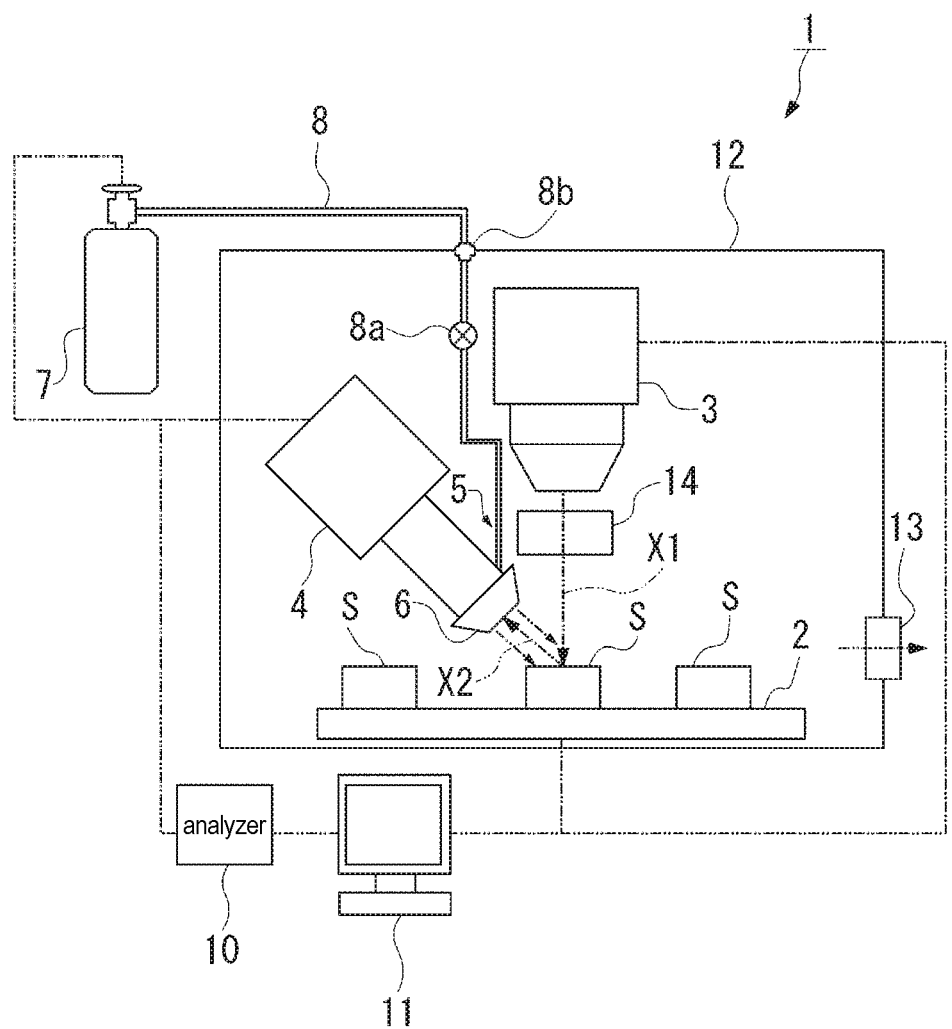
FIG. 1 is a schematic whole configuration diagram showing an illustrative embodiment of the X-ray fluorescence spectrometer of the invention.
Figure 2A:
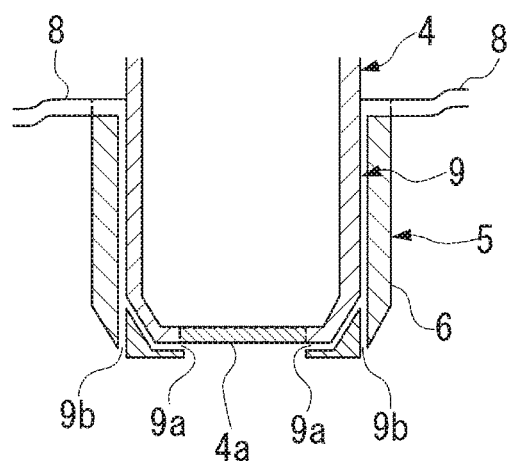
FIG. 2A is a sectional view showing a detector in the illustrative embodiment.
Figure 2B:
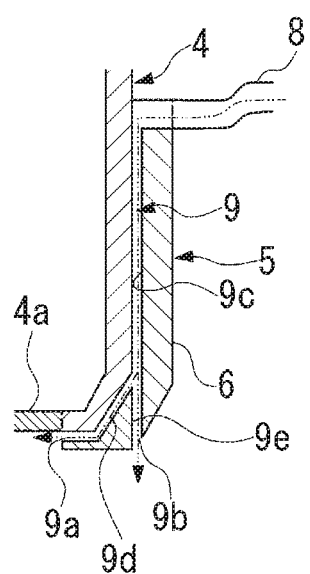
FIG. 2B is an enlarged sectional view of main portions.

As shown in FIGS. 1, 2A and 2B, an X-ray fluorescence spectrometer 1 of the illustrative embodiment includes: a sample stage 2 configured to place a sample S thereon; an X-ray source 3 configured to irradiate the sample S with primary X-rays X1; a detector 4, which is configured to detect fluorescent X-rays X2 produced from the sample S irradiated with the primary X-rays X1, and which has an X-ray incident window 4a formed by a window material through which the fluorescent X-rays X2 can be transmitted; and a gas blowing mechanism 5 configured to blow a gas to the outer surface of the X-ray incident window 4a. The X-ray source 3, the sample stage 2, and parts of the detector 4 and the gas blowing mechanism 5 are accommodated in a housing 12 of the X-ray fluorescence spectrometer 1.

The X-ray fluorescence spectrometer 1 further includes: an analyzer 10, which is connected to the detector 4, and which is configured to analyze a signal supplied from the detector 4; and a control section 11, which is coupled to and controls various components such as the X-ray source 3, the analyzer 10 and the gas blowing mechanism 5, and which is configured to display results of analysis.

The sample stage 2 is a moving stage, on which a plurality of samples S such as a sulfide material is placed, and which is configured to advance to and retract from an irradiation position of the primary X-rays X1 by means of the control section 11.

The X-ray source 3 is an X-ray bulb configured to emit the primary X-rays X1, and in which thermal electrons generated from the filament (cathode) in the bulb are accelerated by a voltage applied between the filament (cathode) and the target (anode), and collide against W (tungsten), Mo (molybdenum), Cr (chromium), or the like of the target to generate X-rays, and the generated X-rays are emitted as the primary X-rays X1 through a window configured by, for example, a beryllium foil. A light condensing device 14 is disposed on the tip end side of the X-ray source 3. The light condensing device 14 such as a monocapillary optic, a collimator, or a polycapillary optic is configured to condense the primary X-rays X1 and to irradiate the sample S with the condensed X-rays.

The detector 4 includes the X-ray incident window 4a formed by a window material through which the fluorescent X-rays X2 is transmittable, and the gas blowing mechanism 5 which blows the gas to the outer surface of the X-ray incident window 4a.

The X-ray incident window 4a is formed by a window material such as Be (beryllium) which is fitted into the tip end portion of the detector 4.

The detector 4 includes a semiconductor detection device (for example, a Si (silicon) device that is a diode having the pin structure) (not shown) which is disposed in the X-ray incident window 4a. In a case where one X-ray photon is incident on the detector 4, a current pulse corresponding to one X-ray photon is generated. The instantaneous current value of the current pulse is proportional to the energy of the incident X-ray photon. Furthermore, the detector 4 is set such that the current pulse generated by the semiconductor detection device is converted to a voltage pulse, the voltage pulse is amplified, and the amplified voltage pulse is output as a signal.

Preferably, the gas to be blown is He (helium). Alternatively, another gas such as the air may be used depending on the sample S.

The detector 4 further includes a collimator section 6, which is disposed in the periphery of the X-ray incident window 4a, for setting an opening degree of the X-ray incident window 4a. The collimator section 6 is formed into a tubular shape and is disposed so as to cover the tip end portion of the detector 4. The collimator section 6 has an opening portion for restricting the opening degree of the X-ray incident window 4a in the tip end thereof.

The gas blowing mechanism 5 includes: a supply source 7 of the gas; a gas pipe 8 in which a base end thereof is connected to the supply source 7; and an internal gas flow passage 9, which is disposed in the collimator section 6, and in which a tip end of the gas pipe 8 is connected to a base end of the internal gas flow passage 9, wherein blow out holes 9a for blowing out the gas are formed in a tip end of the internal gas flow passage 9.

As shown in FIGS. 2A and 2B, the plurality of blow out holes 9a is disposed in the periphery of the X-ray incident window 4a such that the gas can be blown toward the outer surface of the X-ray incident window 4a. The blow out holes 9a are disposed at intervals in the circumferential direction in the periphery of the opening of the tip end of the collimator section 6. All of the blow out holes 9a are directed such that the gas is blown toward inner side.

The supply source 7 is a gas cylinder containing He or the like. The gas pipe 8 is a pipe such as an air tube. A valve 8a for regulating the flow rate is disposed in the middle of the gas pipe 8. In the gas pipe 8, the portions which are outside and inside the housing 12, respectively, are connected to each other via a metal-made gas introduction port 8b attached to the housing 12.

The gas blowing mechanism 5 further includes a mechanism which also blows the gas to the sample stage 2. Namely, the internal gas flow passage 9 includes: a main flow passage 9c, which is connected to the gas pipe 8, and which is formed in a side portion of the collimator section 6; a first branch flow passage 9d, in which a base end thereof is connected to the tip end of the main flow passage 9c, and which is connected to each of the blow out holes 9a; and a second branch flow passage 9e, in which a base end thereof is connected to the tip end of the main flow passage 9c, and which is connected to tip end holes 9b that are opened in the tip end surface of the collimator section 6. The gas flow passage branches off from the main flow passage 9c into the first branch flow passage 9d and the second branch flow passage 9e, and the gas is blown out to the blow out holes 9a and the tip end holes 9b, respectively.

A fan 13 for discharging the gas to the outside is disposed on the side surface of the housing 12.

The analyzer 10 is a multi-channel pulse height analyzer configured to obtain the height of the voltage pulse from the signal to produce an energy spectrum.

The control section 11 is a computer configured by a CPU and the like. The control section 11 includes a display section which can display results of analysis.

In the X-ray fluorescence spectrometer 1 of the illustrative embodiment, in order that the gas is blown to the X-ray incident window 4a, first, the gas blowing mechanism 5 supplies the gas from the supply source 7 to the gas pipe 8. In this case, the flow rate of the gas is adjusted by the valve 8a. In the illustrative embodiment, the gas flow rate is adjusted to 1 to 3 ml/sec.

The supplied gas is introduced from the gas pipe 8 to the internal gas flow passage 9 of the collimator section 6, and then sent from the main flow passage 9c to the first branch flow passage 9d and the second branch flow passage 9e. The gas sent to the first branch flow passage 9d is blown from the blow out holes 9a toward the outer surface of the X-ray incident window 4a.

The gas sent to the second branch flow passage 9e is blown from the tip end holes 9b toward the X-ray irradiation position arranged by the sample stage 2. In this case, by the flow rate control of the valve 8a, the gas is regulated so as to be blown at a speed which does not cause the sample S on the sample stage 2 to be blown off. In the state where the gas is blown from the collimator section 6 toward the X-ray incident window 4a and the sample stage 2 as described above, the sample S is moved by the sample stage 2 to the X-ray irradiation position, and then the X-ray analysis is performed.

As described above, the X-ray fluorescence spectrometer 1 of the illustrative embodiment includes the gas blowing mechanism 5 configured to blow the gas to the outer surface of the X-ray incident window 4a. Therefore, the gas blown toward the X-ray incident window 4a by the gas blowing mechanism 5 is able to prevent the sample S or the like from attaching to the X-ray incident window 4a. Since a MYLAR® film is not used, the characteristic X-rays released from the sample S is not absorbed by a MYLAR® film. Consequently, the sensitivity and throughput of the analysis are improved.

Moreover, the gas blowing mechanism 5 has the mechanism which also blows the gas toward the sample stage 2. Therefore, the sample S on the sample stage 2 can be suppressed from scattering toward the side of the detector 4.

Furthermore, the gas to be blown is He. Since He absorbs less characteristic X-rays than the air, it is possible to obtain a high sensitivity in an analysis of a light element. Moreover, since the gas to be blown to the sample stage 2 is also He, the atmosphere around the sample stage 2 is a He atmosphere, and the absorption of characteristic X-rays is reduced. Therefore, in an analysis of a light element, a higher sensitivity can be obtained. Further, in a case where the sample S is in the form of powder or liquid, which is hardly subjected to measurement under vacuum, high-sensitivity measurement can be performed.

Moreover, the plurality of blow out holes 9a is arranged in the periphery of the X-ray incident window 4a such that the gas can be blown toward the outer surface of the X-ray incident window 4a. By blowing the gas to the X-ray incident window 4a from the plurality of blow out holes 9a arranged in the periphery of the X-ray incident window 4a, it is possible to effectively suppress the sample or the like from attaching to the whole X-ray incident window 4a. Since the internal gas flow passage 9 is formed in the collimator section 6, the gas can be blown by the compact configuration. Therefore, the X-ray fluorescence spectrometer 1 can be placed without reducing the degree of freedom in installation of the detector 4.

The technical scope of the invention is not limited to the above-described illustrative embodiments, and various changes can be made without departing from the spirit of the invention.

The above-described illustrative embodiment is applied to an energy dispersive X-ray fluorescence spectrometer 1 in which the energy and intensity of X-rays are measured by a multi-channel pulse height analyzer 10. Alternatively, the invention may also be applied to a wavelength dispersive X-ray fluorescence spectrometer in which fluorescenc X-rays are dispersed by an analyzing crystal, and the wavelength and intensity of the X-rays are measured.

What is claimed is:

1. An X-ray fluorescence spectrometer comprising:
   a sample stage configured to place a sample thereon;
   an X-ray source configured to irradiate the sample with primary X-rays;
   a detector, which is configured to detect fluorescent X-rays produced from the sample irradiated with the primary X-rays, and which comprises an X-ray incident window formed by a window material through which fluorescent X-rays are transmittable; and
   a gas blowing mechanism comprising a passage extending along a periphery of the detector up to the X-ray incident window and configured to blow gas through the passage to an outer surface of the X-ray incident window.

2. The X-ray fluorescence spectrometer according to claim 1, wherein the gas blowing mechanism comprises a mechanism which also blows the gas to the sample stage.

3. The X-ray fluorescence spectrometer according to claim 1, wherein the gas comprises helium (He).

4. The X-ray fluorescence spectrometer according to claim 1, wherein the detector comprises a collimator section, which is disposed in a periphery of the X-ray incident window, and which is configured to set an opening degree of the X-ray incident window, wherein the gas blowing mechanism comprises:

a supply source of the gas;

a gas pipe, a base end of which is connected to the supply source; and an internal gas flow passage, which is disposed in the collimator section, and in which a tip end of the gas pipe is connected to a base end of the internal gas flow passage, wherein the internal gas flow passage comprises a plurality of blow out holes for blowing out the gas at a tip end of the internal gas flow passage, and wherein the plurality of blow out holes are disposed in the periphery of the X-ray incident window so as to blow out the gas toward the outer surface of the X-ray incident window.

5. The X-ray fluorescence spectrometer according to claim 1, wherein the detector comprises a collimator section, which is disposed in a periphery of the X-ray incident window, and which is configured to set an opening degree of the X-ray incident window, and wherein the gas blowing mechanism comprises an internal gas flow passage, which is disposed in the collimator section, and which is branched off to:

a plurality of first holes disposed in the periphery of the X-ray incident window so as to blow out the gas toward the outer surface of the X-ray incident window; and a plurality of second holes opened in a tip end surface of the collimator section so as to blow out the gas toward the sample stage.

6. An X-ray fluorescence spectrometer comprising:

a sample stage configured to place a sample thereon;

an X-ray source configured to irradiate the sample with primary X-rays;

a detector, which is configured to detect fluorescent X-rays produced from the sample irradiated with the primary X-rays, and which comprises an X-ray incident window formed by a window material through which fluorescent X-rays are transmittable; and a gas blowing mechanism configured to blow gas to an outer surface of the X-ray incident window, wherein the gas blowing mechanism comprises an internal gas flow passage, which is disposed around the periphery of the detector, and which is branched off to:

a plurality of first holes disposed in the periphery of the X-ray incident window so as to blow out the gas toward the outer surface of the X-ray incident window; and a plurality of second holes opened spaced from the plurality of first holes in a direction further away from the periphery of the X-ray incident window so as to blow out the gas toward the sample stage.

7. The X-ray fluorescence spectrometer according to claim 6, wherein the gas blowing mechanism comprises a passage extending along a periphery of the detector to the X-ray incident window.

8. The X-ray fluorescence spectrometer according to claim 6, wherein the gas comprises helium (He).

* * * * *